United States Patent
Hetling et al.

(10) Patent No.: US 7,384,145 B2
(45) Date of Patent: Jun. 10, 2008

(54) MAPPING RETINAL FUNCTION USING CORNEAL ELECTRODE ARRAY

(75) Inventors: John R. Hetling, Dyer, IN (US); Tamas Ban, Round Lake Beach, IL (US); Safa Rahmani, Northbrook, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 11/707,783

(22) Filed: Feb. 15, 2007

(65) Prior Publication Data

US 2007/0188710 A1    Aug. 16, 2007

Related U.S. Application Data

(60) Provisional application No. 60/774,097, filed on Feb. 16, 2006.

(51) Int. Cl.
*A61B 3/00* (2006.01)
*A61B 3/10* (2006.01)

(52) U.S. Cl. .................... 351/219; 351/205
(58) Field of Classification Search .............. 351/205, 351/219, 221, 246
See application file for complete search history.

(56) References Cited

U.S. PATENT DOCUMENTS

| | | | |
|---|---|---|---|
| 4,109,648 A * | 8/1978 | Larke et al. ............ 600/383 |
| 4,131,113 A | 12/1978 | Fender et al. | |
| 4,386,831 A | 6/1983 | Grounauer | |
| 4,874,237 A | 10/1989 | Cringle | |
| 5,297,554 A | 3/1994 | Glynn et al. | |
| 5,506,633 A | 4/1996 | Sperling | |
| 5,886,769 A * | 3/1999 | Zolten ................ 351/219 |
| 6,688,746 B2 | 2/2004 | Malov | |
| 7,018,040 B2 | 3/2006 | Blum et al. | |
| 7,037,943 B2 | 5/2006 | Peyman | |
| 2003/0149350 A1* | 8/2003 | Porciatti ................ 600/399 |
| 2003/0158497 A1 | 8/2003 | Graham et al. | |
| 2004/0039298 A1 | 2/2004 | Abreu | |
| 2005/0119544 A1 | 6/2005 | Valjakka et al. | |

\* cited by examiner

*Primary Examiner*—Scott J. Sugarman
*Assistant Examiner*—DaWayne A Pinkney
(74) *Attorney, Agent, or Firm*—Olson & Cepuritis, Ltd.

(57) ABSTRACT

A system and method for obtaining information about the spatial distribution of photoreceptor activity and neural activity in the retina using simultaneously recorded multiple biopotential signals. The information thus gathered is used to assess retinal dysfunction due to trauma or disease. The biopotential signals are recorded from the surface of the eye and head using a plurality of electrodes, including those integral to a contact lens. The biopotential signals are recorded before, during and after the presentation of an optical stimulus to the subject eye. The recorded biopotential signals are then analyzed and interpreted to reveal the distribution of photoreceptor activity and neural activity across the retina. The analysis and interpretation of the biopotential signals is quantitative, and makes use of an electromagnetic model of the subject eye. The subject may be animal or human.

12 Claims, 11 Drawing Sheets

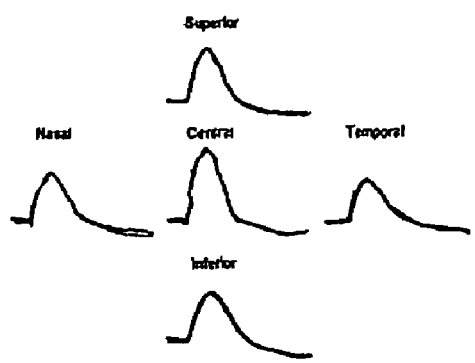
Fig. 2
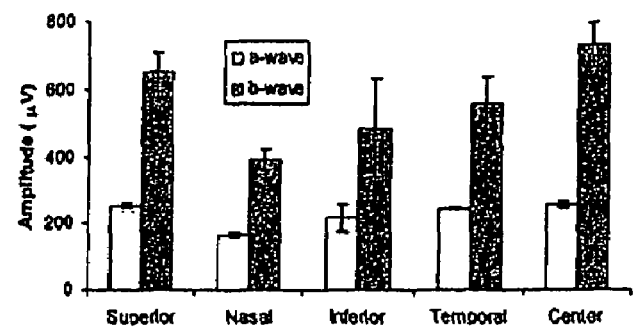
(a)
Fig.3
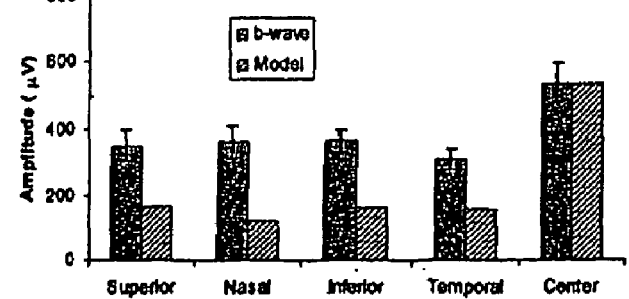
(b)

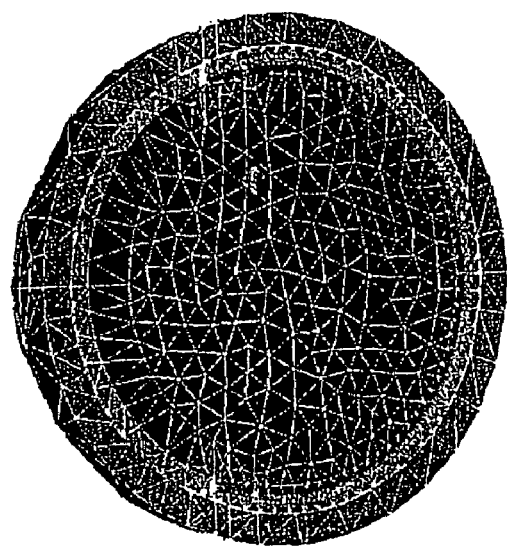
Fig. 4
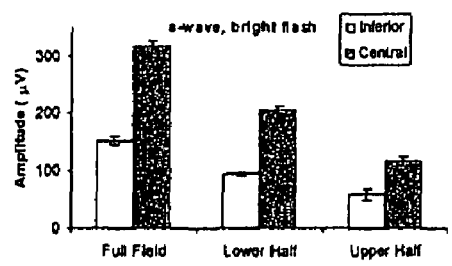
(a)
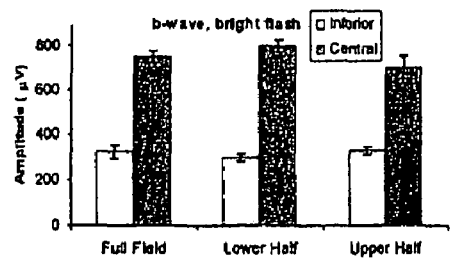
(b)
Fig. 5
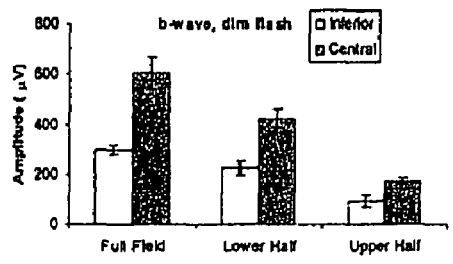
(c)

MAPPING RETINAL FUNCTION USING CORNEAL ELECTRODE ARRAY

CROSS-REFERENCE TO RELATED APPLICATION

This application claims the benefit of U.S. Provisional Application for Patent Ser. No. 60/774,097, filed on Feb. 16, 2006, which is incorporated herein by reference.

FIELD OF THE INVENTION

The present invention relates to local retinal analysis and, in particular, to a system and method for mapping spatial differences in retinal activity using a corneal electrode array to analyze local retinal dysfunction and the presence of eye disease.

DESCRIPTION OF THE RELATED ART

Measurement of the function of the retina, either directly or indirectly, is a central component in diagnosing, assessing and monitoring the progression of dysfunction due to disease or trauma. Indirect measurements of the function of the retina include psychophysical tests, e.g. the Humphrey Visual Field test. Direct measurements include electrophysiological measurements such as the electroretinogram (ERG).

Dysfunction of the retina due to disease or trauma is often localized. Further, early detection is of critical importance in cases of potentially blinding eye diseases, as treatments are directed to slowing or halting progression of vision loss. Therefore measurement of the function of the retina at defined spatial locations on the retina is of great interest.

The Humphrey Visual Field test results in a map of perceptual quality arising from different areas of the retina. However, this psychophysical test has several drawbacks including difficulty in administering the test to young patients or patients with very low vision, and the fact that it measures quality of visual perceptions, and does not directly reflect function at the retina. Further, such psychophysical tests cannot be administered to animals.

Many protocols have been developed to directly measure activity of the retina at defined spatial locations using the ERG. These include the focal ERG and multi-focal ERG. These methods also have significant drawbacks. The focal ERG measures function only in the central retina, and many conditions of great clinical interest (potentially blinding conditions of high prevalence, e.g. retinitis pigmentosa or diabetic retinopathy) first present in the peripheral retina. The multi-focal ERG (mfERG) measures approximately the central 50 degrees of visual field. The mfERG takes several minutes to record, during which the subject must fixate on a small target, making it difficult to record from very young patients or patients with low central vision. Further, the mfERG signal is not a true bioelectric signal, and physiological interpretation of the signal remains a challenge.

As mentioned, eye diseases often result in localized dysfunction of the retina. In a clinical setting, electroretinography is a useful, non-invasive procedure for determining spatial differences in retinal activity in which electrical potentials generated by the retina of the eye are measured upon exposing the retina to a light stimulus. An electroretinographic recording, referred to as an electroretinogram, is typically abbreviated as ERG. In conducting an ERG, an electrode is positioned on the cornea of a patient's eye and a second electrode, usually referred to as an "indifferent" electrode is positioned to complete an electrical connection with the patient's upper anatomy. The indifferent electrode may be placed, for example, in the mouth or may be electrically coupled to the patient's ear or other convenient locus for such connection. The retina is then exposed to a light source and, in response, generates one or more electrical signals which are then studied. An ERG is a record of the resulting electrical signals.

Illumination may be conducted in a number of ways. For example, a first set of electroretinogram readings may be taken in normal room light. In a second step, the lights may be dimmed for a significantly long period of time (on the order of 20 minutes), and readings are taken while the patient's retina is exposed to a light source. That is, after prolonged relaxation in a dark environment, electrical retinal readings are taken at the onset of retinal exposure to light, and for a time period shortly thereafter. As a further step, after a sufficient time for relaxation has passed, a bright flash may be directed to the patient's retina with further electroretinogram readings being taken. Each electroretinogram reading will differ depending upon the light conditions to which the patient's retina is subjected. However, standard responses have been established for each type of test and various useful conclusions can be drawn from excursions from such standardized data. In each test, the retinal response to each illumination is typically in the form of voltage versus time waveforms. Different types of waves have been defined for normal retinal responses. It is expected in a healthy patient, for example, that an electroretinogram shows a-wave and b-wave patterns normal in shape and duration, with appropriate increases in electrical activity as the illumination intensity is increased.

It is understood that the electrodes measure the electrical responses of individual rods and cones which are constituents of the human retina located at the back of the eye. The rods and cones comprise visual cells which "convert" or otherwise respond to illumination with electrical activity. This electrical activity is preferably measured with minimum invasion to the patient's anatomy, by placing an electrode on the patient's cornea. As indicated above, the electrode may be mounted on a contact lens for convenient application in an outpatient setting. Such an electrode typically measures summed activity from the retina. In general, the electrical changes caused by the different major cell types comprising the retina (rod and cone photoreceptors, bipolar cells, horizontal cells, amacrine cells, ganglion cells, Muller cells) tend to overlap, thus the complex and varying waveform. The most prominent wave is the b-wave and the height of this wave can provide an indication of the patient's sensitivity to the illumination source. Tests can be conducted with illumination sources of different spectral content, intensity, kinetics, spatial patterns and spatial contrast, and the results can be studied to determine the patient's medical condition.

The idea of local neural activity in the retina being correlated with local potentials recorded from the eye or face has been described by several groups. The first analytical account of the electric fields generated by retinal activity was given by Krakau [1958], who compared potentials recorded across a rabbit cornea with model predictions. The computational approach used Helmholz's theory of electromotive surface to estimate the potentials at the corneal surface. The equations assume radial symmetry, and do not account for any ocular structures, modeling the eye as a perfect sphere. Doslak, Plonsey and colleagues extended this work by incorporating the major ocular structures (sclera, cornea, lens), but maintained the assumption of axial symmetry (and therefore reduced the model to two dimensions) [Doslak et al., 1980; Doslak et al., 1981]. This work necessarily used numerical methods to accommodate the anatomical detail (Laplace's equation and an iterative finite-difference algorithm) to solve for the potential at approximately 1000 nodes empirically distributed across one half of one slice through the eye. A significant result was the demonstration of the influence of the R-membrane resistance on the ERG. Job et al. [1999] extended the model of Doslak to three dimensions (same anatomical detail as [Doslak et al., 1980]), and used a similar finite difference approach (node values calculated from six nearest neighbors, convergence hastened using a successive over-relaxation method). Plausible predictions of corneal potentials were made for uniform retinal activity, central and peripheral focal stimuli, and central and peripheral focal scotomas, however validation of the model was primarily by comparison to other models. The purpose of this study was to evaluate the use of a single electrode location with the mfERG technique, with the conclusion that different retinal locations contributed differently to local corneal potentials, and that electrode configuration should be optimized.

The empirical finding that the human cornea is not isopotential has been described by Gouras et al. [1962]. This finding suggested that these spatial differences in source potentials could be used to infer the spatial distribution of the source (i.e. spatial differences in activity of the retina). This idea of source modeling from ERG potentials to create a functional map of retinal activity has also been explored in the literature. The efforts of Doslak et al. described above were primarily concerned with the forward problem (predicting corneal potentials from retinal source activity). Davey et al. [1988] first attempted to solve the inverse problem, predicting retinal source activity from measured corneal potentials. Their methods were essentially those of Doslak extended to three dimensions, but with an ultra-simplified model structure, consisting of an oval of uniform conductivity (the eye) in contact with bulk extra-ocular tissue on one side and air on the other (ignoring the lens and finite thickness of the sclera and cornea). Corneal potentials were evaluated at 6 locations, and retinal activity predicted in 6 broad regions. When using ERG responses recorded following a full-field stimulus (in frog) as the model input, the predicted retinal source currents were low in central regions, typical in mid-regions, and entirely inverted in peripheral regions. These predicted spatial differences in retinal activity are irreconcilable with current knowledge of distributed retinal activity, and most likely reveal the serious limitations of the oversimplified model. Davey et al. conclude that, "The multiple measurement single stimulus [approach] has a sound theoretical foundation . . . spatial resolution is linked intimately to the amount of information one can extract from the cornea . . . practical application could only be realized by use of a delicate contact lens having multiple implantable electrodes . . . " Thus, the need exists for such a contact lens. One drawback of existing systems is that they are designed to infer local physiological activity in the retina from biopotential recordings use single electrodes, or single bipolar pairs of electrodes, located on the eye surface, in combination with a spatially-variant optical stimulus (e.g. a focal spot, an array of hexagons, a checkerboard). Thus the need exists for a system which can take advantage of a full-field, spatially invariant stimulus.

Different types of electroretinography are currently used. One type is the pattern electroretinogram (PERG) which tracks the retinal response made in response to viewing an alternating grating pattern such as that of a checkerboard arrangement. The pattern is modulated over time so as to produce a constant luminance during the test. The PERG test is frequently carried out with a checkerboard pattern which is alternately reversed. This type of test is used in clinical and research programs in both ophthalmological and neurological practice. The International Society for Clinical Electrophysiology of Vision has prepared a standard for a basic PERG recording procedure which is helpful in obtaining standardized responses.

Another type of non-evasive method to measure spatial differences in retinal function is the multi-focal electroretinogram (mfERG). This method is limited in several significant ways. First, stimulus dynamics inherent to the mfERG technique limit measurements to primarily cone-pathways activity. Second, the output of the mfERG system is a mathematical abstraction of the recorded activity of the retina, which has limited interpretation at present, and which can thus be misinterpreted or over-interpreted. In addition, the mfERG test is difficult to administer to patients with low vision or to small children because the patient must fixate on a small visual target for several minutes of continuous data acquisition. Additional minor limitations include the restricted area of retinal evaluation (typically covering the central 50 degrees of the field of vision) and the relatively high cost which restricts access to the testing procedure. Thus, a need exists for improved full-field testing.

There is no known prior art system involving a contact lens electrode array. Also, there is no known prior art system involving the use of biopotentials recorded from multiple locations on the cornea, or from the cornea plus the sclera and/or face and/or scalp, to infer spatial differences in physiological activity of the retina. U.S. Pat. No. 4,874,237 describes the use of four electrodes placed on the sclera of the eye, outside the corneal limbus, to record simultaneous ERG biopotentials for the purpose of identifying regions of dysfunction in the retina. This idea was described in [Cringle and Alder, 1987] and [Cringle et al., 1986]. The present invention is novel in that it uses multiple electrodes located on the cornea, and additional electrodes on the sclera, face or scalp. The present invention also includes a quantitative method to infer spatial differences in activity of the retina from biopotentials recorded at multiple locations.

SUMMARY OF THE INVENTION

In one aspect, the present invention provides an improved method for mapping spatial differences in retinal activity, using a full-field stimulus, especially one that is spatially invariant, and an electrode array in contact with a patient's cornea. This method is an improvement over multi-focal ERG and pattern ERG which both require specialized stimulus sources. A computational method is also provided for use in analyzing the bioelectric activity of the retina from potentials recorded at the cornea. This method provides an array of electrodes, and places the electrodes in electrical contact with the cornea. While illuminating the eye so as to cause retinal activity, measurements are made of the electrophysiological potentials at the cornea in response to the illumination with the array of electrodes. The method concludes by solving for retinal information based on the electrophysiological potentials made at the cornea.

In one example, the present invention uses standard full-field stimuli in conjunction with a corneal multi-electrode array. Spatial ERG data are then correlated with the region and degree of retinal dysfunction. In addition to the corneal electrode array, an appropriate analysis or source modeling of the collected data provides information regarding the location and extent of retinal dysfunction. Results are achieved using standard electrophysiology amplifiers and digital data acquisition systems. Software unique to the present invention accomplishes the source modeling.

In another aspect, the present invention provides a method of obtaining an electroretinogram by providing an array of electrodes, and positioning the array of electrodes on the surface of a patient's eye so that at least some of the electrodes contact the patient's cornea. In one example, five or more electrodes are used, but other numbers of electrodes can also be used if desired. While illuminating the patient's eye, preferably with full-field, spatially invariant stimulation, the array of electrodes is monitored for electrical activity of the eye in response to the illumination. Preferably, the patient's eye is illuminated by passing light through or past the array of electrodes, and accordingly it is desirable in certain instances, to make the array of electrodes at least partially transparent to the illumination. If desired, the array of electrodes can comprise an openwork array of spaced apart conductive members carried on a dielectric carrier, such as a corneal contact lens. The electrodes are preferably carried on the inner surface of the contact lens, so as to contact the corneal surface.

In another example, the present invention provides an electrode for electroretinography in which a contact lens body has an outer periphery, an inner surface facing the patient's eye and an opposing outer surface. An array of conductive members carried on the inner surface of the contact lens body so as to be integral therewith. The conductive members and the contact lens body can be made of virtually any suitable material, as may be desired. The array of conductive members is positioned about the contact lens body so that at least a portion of the conductive members contacts the patient's cornea, although the sclera may also be contacted, as well. The conductive members are either spaced apart from one another or are made sufficiently thin so as to be substantially transparent to full-field stimulation of the patient's eye, so as to permit a substantial amount of the full-field stimulation to reach the patient's retina. The conductive members extend to the outer periphery of the contact lens body, and connections to the conductive members are provided at the outer periphery so as to be integral with the contact lens body. Preferably, at least five conducting members are carried on the contact lens body.

A lead assembly is also provided in another aspect of the present invention. The lead assembly includes the electrode described immediately above, in combination with an array of skin electrodes that either surround the eye, or are in contact with the scalp.

A system and method are also provided for obtaining an electroretinogram utilizing an array of electrodes positioned on the surface of a patient's eye. The array of electrodes is at least partially transparent to illumination which passes through the front surface of the patient's eye to reach retinal components located at the back of the eye. The array of electrodes is monitored for electrical activity of the patient's eye in response to the illumination. In one embodiment, the array of electrodes comprises an array of conductive members, such as gold particles or another noble metal, carried on the surface of a contact lens of dielectric material such as PMMA [poly(methyl methacrylate)].

The present invention, in another aspect, also provides a finite-element model of the eye for use in analyzing the bioelectric activity of the retina for potentials recorded at the cornea. The model includes determining anatomical structures of the eye and tissues and materials surrounding the eye, and determining electrical properties of each structure. Retinal activity is stimulated via a time-varying change in the electrical activity either within or across the retina. In one example, the electrical activity comprises a time-varying change in charge distribution or local currents within or across the retina.

In another aspect, the present invention provides an assembly for electroretinographic recording. The assembly includes a contact lens body having an outer periphery, an inner surface facing the patient's eye and an opposing outer surface. A first array of recording electrodes is positioned on the inner surface of the contact lens body so as to contact the cornea. The electrodes of the first array are spaced apart from one another and are substantially transparent to full-field stimulation of the eye thereby permitting a substantial amount of full-field stimulation to reach the cornea. The first array of recording electrodes extends to the outer periphery of the contact lens body where connections are provided for electrical connection to external electrical circuitry. A second array of recording electrodes is in contact with either the scalp or the skin surrounding the eye. Electrical leads connect the first and the second arrays of recording electrodes to external circuitry that receives responses detected by the recording electrodes.

BRIEF DESCRIPTION OF THE DRAWINGS

FIG. 1a shows a typical stimulus arrangement for a multi-focal ERG. FIG. 1b shows calculated waveforms ascribed to the areas of the retina responsive to each hexagon in the stimulus. FIG. 1c shows a proposed model for interpreting the cellular origin of the waveform components.

FIG. 2 shows multi-electrode electroretinogram (meERG) waveforms recorded at five locations on the left cornea of a rat.

FIG. 3 shows electroretinogram potentials measured at different locations on a patient's eye. FIG. 3a shows meERG potentials measured at 5 locations on the cornea. FIG. 3b shows meERG b-wave potentials evaluated at peak following a dim flash, compared with corresponding model predictions of corneal potential.

FIG. 4 shows three-dimensional finite element model of a rat eye, shown in cross section and slightly rotated.

FIGS. 5 shows a comparison of potentials measured at two locations on the cornea.

DETAILED DESCRIPTION OF THE PREFERRED EMBODIMENT

Figure 1:
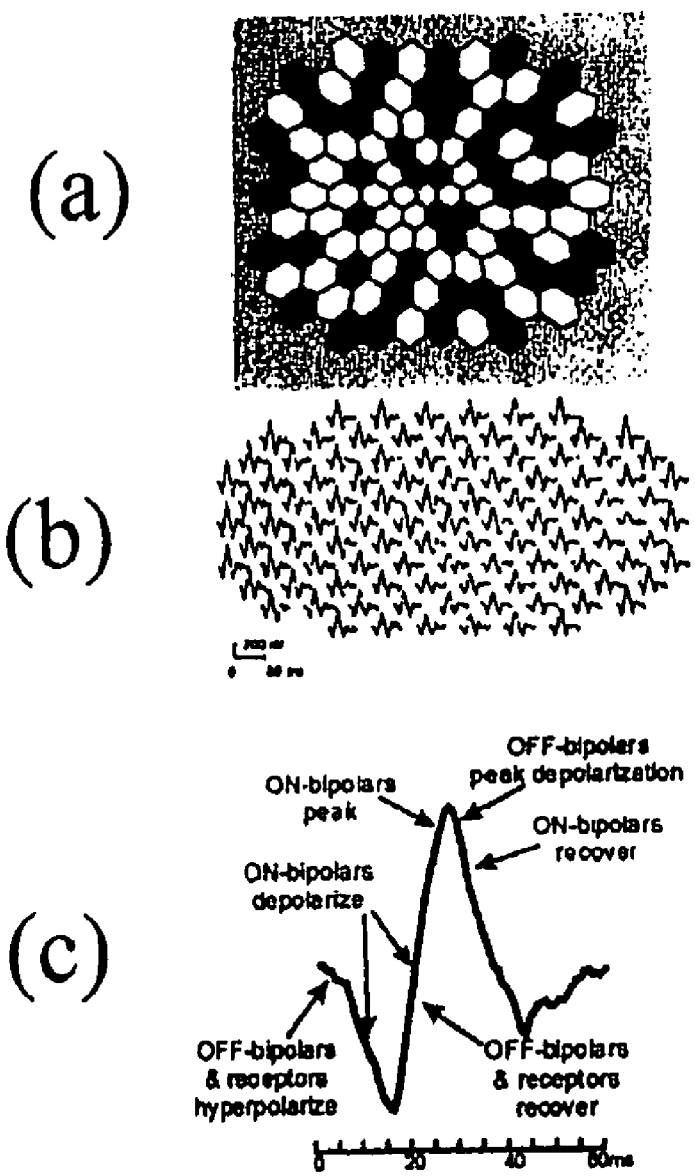
FIGS. 1a-1c contain schematic drawings showing different aspects of an analytical study.

The invention described herein is, of course, susceptible of embodiment in many different forms. Shown in the drawings and described hereinbelow in detail are preferred embodiments of the invention. It is understood, however, that the present invention in an exemplification of the principles of the invention and does not limit the invention to the illustrated embodiments. For ease of description, different arrangements embodying the present invention are described hereinbelow in their usual assembled position as shown in the accompanying drawings, and terms such as upper, lower, horizontal, longitudinal, etc. may be used herein with reference to this usual position. However, the arrangements may be manufactured, transported, sold or used in orientations other than that described and shown herein.

New systems and techniques are provided for measuring local activity in the retina and, if desired, may be used with existing techniques. A brief review of electroretinography and the primary complimentary technique, the multi-focal electroretinogram, are set out, followed by a brief discussion of functional mapping from recorded body-surface potentials, as developed for heart and brain. These approaches to functional mapping are exemplary of techniques which can be used with the present invention.

An electroretinogram (ERG) is a bioelectric signal arising in the retina, and is recorded in response to a light stimulus. In a clinical setting, an ERG is recorded using non-invasive means, where the active electrode is integral to a contact lens that allows an unobstructed view of the stimulus source. A corneal ERG is a potential reflecting the summed contribution of all retinal cells responsive to the stimulus. The most typical type of stimulus is a brief (<1 ms) full-field flash, where the stimulus has constant luminance across the entire visual field.

Many variations of ERG recording have been developed, which can be separated into two categories (see Lam [2005] for an overview). In the first group, the dynamics of the stimulus are altered to exploit temporal response properties of specific functional retinal circuits or cell types. One example is the flicker ERG, in which light flashes are delivered in rapid succession (~30 Hz), eliciting responses from fast-recovering cone-pathways in the retina (the rod pathways do not have sufficient time to recover between the rapid flashes, and are thus saturated by the time-averaged luminance of the source). A second example is the paired-flash ERG, in which the stimulus flash is followed at a defined time t by a bright probing flash, which drives retinal photoreceptors to saturation and thus titrates the level of response due to the stimulus flash at time t [Hetling and Pepperberg, 1999].

The second group includes ERG techniques in which the geometry of the stimulus is varied (from the typical full-field) in order to probe local areas of the retina. The two most common techniques in this category are the focal ERG and the multi-focal ERG. The focal ERG consists of a focal spot stimulus typically delivered via a hand-held ophthalmoscope with integral stimulus source. The spot is directed by the investigator or clinician to an area of interest, usually the fovea, and the response is recorded with a standard corneal electrode. The spot is illuminated in rapid succession (30-42 Hz), and the area of interest is surrounded by a ring of bright constant illumination to avoid contributions due to scattered light outside of the area of interest.

The focal ERG and the multi-focal ERG methods are comprised of focal stimuli to the retina and recording the ERG signal from a single electrode, or bipolar pair of electrodes, at the eye surface. By contrast, the invention described here uses a full-field, homogeneous, preferably spatially invariant stimulus and an array of recording electrodes placed on the eye and head. Surface potentials are recorded simultaneously from several locations on the eye and head, and these signals are then analyzed and interpreted to create a map of the signal source distribution across the retina. This is analogous to functional brain mapping using an array of scalp electrodes to record the electroencephalogram, or functional cardiac mapping using an array of chest electrodes to record the electrocardiogram.

Multi-focal ERG (mfERG) has become more common than the focal ERG in recent years. The mfERG stimulus is a field of contiguous hexagons (typically 103, subtending the central 50° of visual field, upper panel of FIG. 1a), which are scaled to elicit approximately equal amplitude responses from a normal retina. Each hexagon alternates between high and low luminance (e.g. 100 cd m$^{-2}$ and 2 cd m$^{-2}$, commonly described as white and black) in a predefined, pseudo-random temporal sequence called an m-sequence. Each hexagon follows the same sequence, but each starts at a different point in the m-sequence, and each has a probability of changing from white to black of 0.5 at each transition time. Transitions occur at approximately 75 Hz.

FIG. 1a, referred to above, shows a typical stimulus arrangement for a multi-focal ERG. As will be seen herein, FIG. 1b shows calculated waveforms ascribed to the areas of the retina responsive to each hexagon in the stimulus, and FIG. 1c shows a proposed model for interpreting the cellular origin of the waveform components. Adapted from Lam [2005].

Multi-focal ERG (mfERG) data are collected with a known ERG contact lens electrode, having either a single electrode, or multiple electrodes. Regardless of the type of electrode system used, the eye responds to the applied stimulus, and the response is recorded continuously. As will be seen herein, contact lens assemblies according to principles of the present invention overcome many of the deficiencies of known ERG contact lens electrodes. In the mfERG technique, a mathematical correlation ascribes a portion of each response to each hexagon. The data are analyzed in several ways with respect to the temporal relationship to transitions in the m-sequence. The most straightforward analysis is to evaluate the waveform immediately following any transition from black to white, the so called first-order response, or first-order kernel. The responses following a black frame are summed and subtracted from the sum of all responses following a white frame. The resulting first-order response has a duration that exceeds the transition interval. The result is an array of mfERG waveforms corresponding to the areas of retinal responsive to each hexagon (FIG. 1b).

Other analysis strategies are also used, including the first and second slices of the second order response, which simply generate responses that are correlated with events farther back in the m-sequence. All of the mfERG responses are mathematical abstractions of the bioelectrical events, and while progress has been made in understanding the functional origin of each response component (FIG. 1c), the waveforms are still incompletely understood, especially the second and higher order kernels. Regardless of the analysis kernel, only cone pathways are responsive to the mfERG stimulus due to the relatively high time-averaged luminance (which saturates the rod-pathways). Some progress has been made in adapting the mfERG to evaluate rod pathways [Hood et al., 1998], but the method is difficult to implement, requiring careful optimization of light levels.

mfERG is commonly used to assess pathology of the inner (glaucoma [Chan, 2005], diabetic retinopathy [Tyrberg et al., 2005]) and outer (retinitis pigmentosa [Seiple et al., 2004], heredofamilial macular degenerations, choroidal ischemia/inflammation [Holder, 2004], age-related macular degeneration [Feigl et al., 2005]) retina. The principal disadvantage of the mfERG is the limited flexibility in stimulus dynamics (so that only cone pathways are easily evaluated). The multi-electrode ERG (meERG) technique disclosed herein overcomes this disadvantage. meERG employs a standard full-field stimulus, and would allow the use of nearly any arbitrary stimulus dynamics, including standard scotopic flashes under dark-adapted conditions (to evaluate rod pathway function, critical in evaluation of night blindness), paired-flash protocols (to isolate temporal aspects of rod or cone photoreceptor function), step stimuli (to study the on-response), and saw-tooth waveforms (either rapid-on or rapid-off, to study on and off responses, respectively [Alexander et al., 2001]).

Further, each of the unique response waveforms obtained with the stimuli described above are entirely equivalent to those recorded under standard ERG conditions, and could be analyzed with no special consideration of the meERG technique. This is in contrast to the mfERG waveforms, which are mathematical abstractions of the underlying physiological signals and are less well-understood than directly recorded full-field ERG responses [Hood et al., 2002].

Another limitation of the mfERG technique addressed by the meERG approach is the limited area of the retina responsive to the mfERG field of hexagons (the central 50°). This hinders evaluation of peripheral dysfunction, critical to early detection of pathologies that begin in the periphery such as retinitis pigmentosa.

The limitations of mfERG, and the potential benefits of meERG according to the present invention, make these two techniques complimentary to one another. The advantages of mfERG are good spatial resolution (typically 3-7° of visual angle for a typical 103-hexagon array) and a significant and growing amount of experience with the technique. A common theme in functional mapping of brain and cardiac tissue is multi-modal imaging, where two measurement techniques of complimentary strengths are used together (e.g., high spatial resolution fMRI scans combined with high temporal resolution EEG source modeling [Babiloni et al., 2005]). The combined use of mfERG and meERG exploits the established high spatial resolution of the mfERG with the functional specificity of the meERG.

An additional limitation of mfERG is the substantial cost of these systems ($50k-$100k for the VERIS-System, depending on features, from Electro-Diagnostic Imaging). This makes the assessment of local retinal activity inaccessible to many smaller research labs and clinics. While meERG is not being proposed as a substitute for mfERG, its cost will be substantially lower. To convert an existing, standard full-field ERG system to the meERG technique only requires a relatively inexpensive contact lens, open wire or other electrode array, appropriate amplifiers and data acquisition hardware, and the software for solving the inverse problem (i.e., multiple electrodes used with a simple light source). Any lab that has an mfERG system could easily integrate the complimentary meERG. Therefore, the availability of the meERG technique here, provides a substantial advantage for financially challenged clinics.

Previous Efforts in Functional Mapping. There is an extensive history of functional mapping of the brain and heart using a variety of techniques. The approach most relevant to this method is the use of potentials measured by an electrode array on the body surface. These data are used to predict the properties of the bioelectric sources (the inverse problem) via a vast variety of techniques, including closed-form solutions for idealized volume conductors, Laplacian mapping (use of second spatial derivative of surface potentials), template matching algorithms, finite element model optimization, boundary-element techniques, and combinations of these methods. Davey et al. [1988] attempted a closed-form solution to predict contributions to the electroretinogram based on the earlier efforts of Plonsey [Plonsey, 1984; Doslak et al., 1980]; these are examples of literature describing the use of local ERG potentials to describe spatial retinal activity. Results showed promise for using corneal potentials, but the geometrical simplifications required by the analytic solution reduced the potential accuracy of this approach. There is a variety of techniques available for source modeling (see He and Lian, 2002; and He and Wu, 1999, for reviews of functional brain and cardiac mapping, respectively).

A valid, straightforward method of initial template matching, followed by nonlinear regression to minimize an error measure, is useful in the present invention. This approach is relatively easily implemented for the complex geometry of the model. The solution method is not the limiting factor in performance of the meERG method; as the number of electrodes exerts more serious constraints. A significant impediment to source modeling for the brain and heart is the spatial low-pass filtering effect of the large volume conductor present between the source and body-surface electrodes, and in particular the low-conductivity skull in the case of brain mapping. The eye is less affected by these limiting factors, as the distance between the electrodes and source is relatively small, and the intervening structures display relatively good conductivity.

Preliminary Results

Advantages of the meERG technique are explored with two key experimental findings: (a) spatially-varying potentials can be recorded at the cornea; that is, the corneal surface is not isopotential (even for uniform retinal illumination) and (b) spatial variations in retinal activity result in corresponding measurable changes in corneal potentials. Both of these findings are documented herein below. Analysis of corneal potentials to determine the spatial distribution of retinal sources (i.e. functional mapping of the retina) requires a computational model of the eye, and an appropriate algorithm to solve the inverse problem. Such a model has been constructed, and agrees qualitatively with the experimental findings, also detailed below.

Spatially-Varying Corneal Potentials. Using standard ERG techniques with rat eyes (methodological details summarized at the end of this section), spatially-varying potentials at the cornea are obtainable. In one example, a platinum recording electrode about 0.5 mm in diameter is placed at five distinct locations on the cornea; at each location the response to a single homogeneous full-field flash stimulus is recorded (FIG. 2).

FIG. 2 shows meERG waveforms recorded at five locations on the left cornea of a rat. Flash strength=0.01 scotopic candela seconds per meter squared (sc cd s m$^{-2}$). Locations as labeled; the recording electrode was placed approximately 0.5 mm central to the limbus at each peripheral position. Each waveform plotted in the Figure is the average of 5 responses recorded in a pseudo-random order.

The meERG waveforms are recorded in response to two different flash strengths and are analyzed for a-wave and b-wave amplitudes, and the results plotted in FIGS. 3a and 3b. FIG. 3a clearly demonstrates the variation in signal amplitude as a function of electrode location, which is repeatable from measurement to measurement and between animals (n=4).

Figure 16:
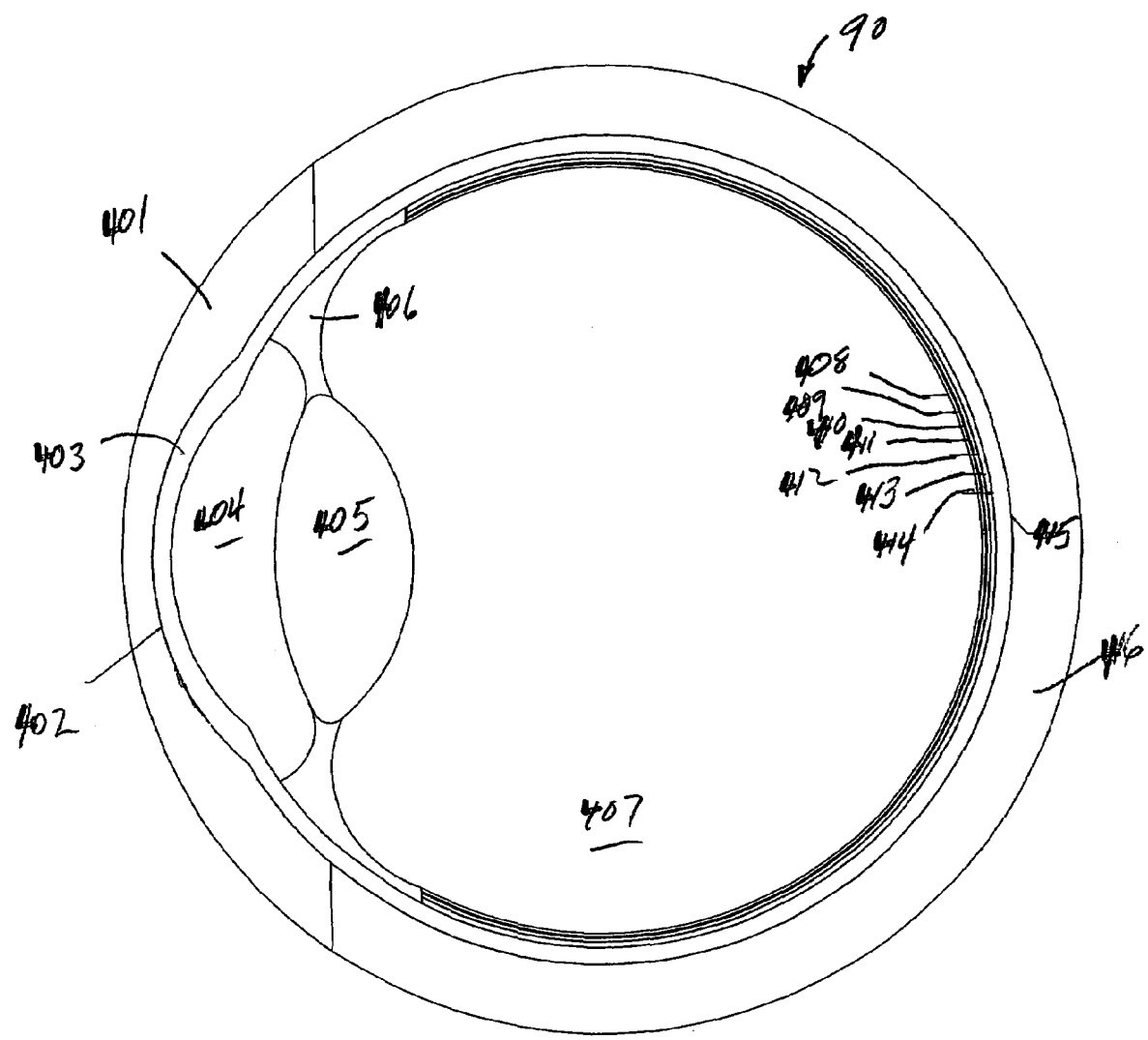
FIG. 16 shows a schematic representation of a model of the human eye.

FIG. 3 shows electroretinogram potentials measured at different locations on a patient's eye. FIG. 16 shows a model of a human eye generally indicated at 90. Included in the model is an airspace 401 and an anterior tear film 402 located in front of a cornea 403. An anterior chamber 404, a lens 405 and vitreous humor 407 lie behind the cornea, as shown. A ciliary body and zonule fiber 406 are located at either side of lens 405. As indicated at the right hand end of FIG. 16, the interior of the eye includes a retinal nerve fiber layer 408. Reference number 409 refers to the neural retina, including the ganglion cells, amacrine cells, horizontal cells, bipolar cells and Muller cells. An outer limiting membrane 410 lies in front of the array of rods and cones indicated at 411. Numeral 412 refers to the retinal pigments epithelium/R-membrane. Also included is a choroid 413 and a sclera 414. Posterior tear film is indicated at 415 and adipose/muscle tissue is indicated at 416. FIG. 3a shows meERG potentials measured at 5 locations on the cornea (see FIG. 2). a- and b-wave amplitudes were evaluated at peak following delivery of a bright flash (54 sc cd s m−2). The a- and b-wave potentials are not uniform across the cornea, and scale similarly at each position (R2 =0.91). FIG. 3bshows meERG b-wave potentials evaluated at peak following a dim flash (0.01 sc cd s m−2), compared to model predictions of potential at the same locations on the cornea. Model amplitudes were scaled to the maximum measured potential. In both Figures, bars plot means +one standard deviation, n=10 flashes presented in one experiment.

An interesting phenomenon seen consistently is that the meERG potentials do not exhibit the same relative amplitudes for different flash strengths. Compare b-wave amplitudes in the upper (bright flash) and lower (dim flash) FIGS. 3a and 3b. The relative amplitudes for a- and b-waves in response to the bright flash (FIG. 3a) are highly correlated ($R^2$=0.9), but distinct from those measured in response to the dim flash (FIG. 3b). This implies that the spatial activity of the retina and/or the spatial summation of potentials at the cornea is a function of flash strength.

One possible explanation is the difference in relative contribution between the inner and outer retina for the two flash strengths, due to the physiological amplification of the visual signal by the bipolar cell layer, and due to the existence of the outer limiting membrane (OLM), a high-impedance barrier formed by junctions between Muller cells and other Muller cells, and between Muller cells and photoreceptor cells (desmosomes or zonula adherens) at the level of the photoreceptor inner segments. The cellular origin of the a-wave (photoreceptors) is distal to the OLM compared to the cellular origin of the b-wave (bipolar cells). This hypothesis is tested using the model (described below) by simulating two biopotential sources, one distal to the OLM (representing photoreceptor contributions) and one proximal (representing inner-retinal contributions). This important difference impacts the algorithm used to solve the inverse problem, essentially requiring two solutions, but allows appropriate analysis of both inner and outer retinal function.

Figure 17:
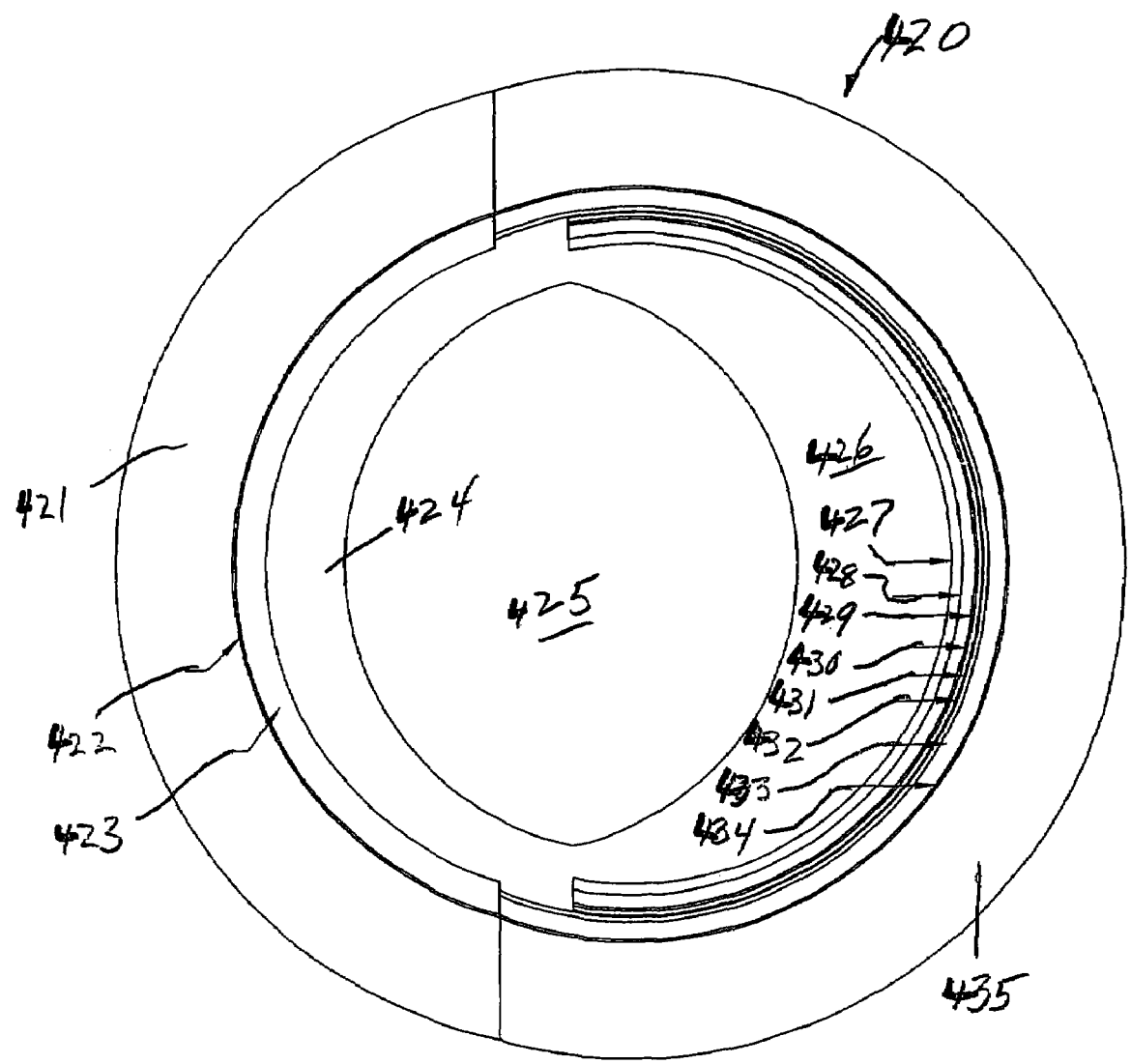
FIG. 17 shows a schematic representation of a model of a rat eye.

Computational Model of the Rat Eye. The spatial variation of corneal potentials, using a 3-D finite element (FE) model of a rat eye, is predicted. Geometry of the major ocular tissues (sciera, choroid, retina, vitreous, lens, anterior chamber, cornea) is based on a standard rat schematic eye [Hughes, 1979;Monte's-Mico, 2005]; a thin tear film that completely surrounded the eye and a layer of adipose tissue surrounding the eye posterior to the limbus is also included. As can be seen with reference to FIG. 17 which depicts a schematic diagram of a model of a rat eye, indicated generally at 420. Included in the model is an air layer 421, anterior tear film 422 and a cornea 423. An anterior chamber 424 and lens 425 lie behind cornea 423. Vitreous humor is indicated at 426. A number of structures are indicated by reference numerals appearing at the right hand end of FIG. 17. Included, for example, is a retinal nerve fiber layer 427 and a region located at 428 indicating the neural retina, including the ganglion cells, amacrine cells, horizontal cells, bipolar cells and Muller cells. An outer limiting membrane is indicated at 429 and the rods and cones are indicated at 430. Reference numeral 431 indicates a retinal pigment epithelium/R-membrane. The choroid and sclera are indicated at 432, 433. A posterior tear film is indicated at 434 and adipose/muscle tissue are indicated at 435.

Additionally, two high-impedance structures which shape the ERG response were simulated: the outer limiting membrane (OLM), and R-membrane (retinal pigment epithelium). The model geometry is defined in Solid Works 2001, converted to Initial Graphics Exchange Specification (IGES) format, and then imported into ANSYS 9.0 Multiphysics with EMag where conductivity of the various tissues and tear film is assigned (100 Hz conductivity values taken from the literature [IFAC, 2002], see Table 1 below). Solid 3-D, 10-node, charge-based electric elements (Solid123) is used to mesh the model to a resolution of 0.2 mm. Solid123 is chosen as it is well suited to model irregular meshes (such as curvatures of the eye). This element has only one degree of freedom, node voltage. The model comprises 107,630 nodes and 79,601 elements. The h-method discipline is used to carry out the low frequency (100 Hz) electrostatic simulation to compute meERG potentials. The eye, with surrounding tear film and adipose tissue, is further surrounded by a layer of air which forms the boundary of the model. The bioelectric source in the model is defined as a separation of charges across the retina (distal surface served as "ground") that varies as a sine wave of frequency 100 Hz (a significant frequency in the ERG bandwidth). The magnitude of peak charge density (1395 $C/m^2$) was chosen such that the resulting peak-to-peak potential at the corneal pole is 100 μV (a typical ERG peak amplitude). Local areas of retinal dysfunction were simulated by reducing the amplitude of the sine wave in defined areas of the retina (unless otherwise stated, to zero in results reported here).

Comparison of Model and Measurements with Uniform Retinal Activity. The model just described is used to predict the potentials at different locations on the cornea, evaluated at the tear film surface (electrodes typically make electrical contact with the cornea through a lubricating layer of tears or ophthalmic methylcellulose). One comparison between model results and experimental measurement appears in FIG. 3b. Here, and in FIG. 6 below, the model results are normalized to the largest response recorded experimentally. At each of the five locations on the cornea, there is a general agreement between this first approximation model (no attempts to optimize the model based on experimental measurements are made) and the measured values of corneal potentials.

Experimental Simulation of Retinal Dysfunction. The meERG technique maps spatial variations in retinal activity based on recording potentials at the cornea. This requires that changes in retinal activity be reflected in measurable differences in the corneal potentials. A significant level of retinal dysfunction is experimentally simulated by providing an approximately half-field stimulus. This is accomplished by placing an opaque card over half of the backlit screen that serves as the luminous stimulus source. In theory, only one half of the retina will be illuminated, but due to light scatter and uncertain accommodative state, it more likely results in a significant but not complete reduction in retinal illuminance over one half of the retina, with an indistinct border between the two conditions. FIG. 5 presents the results of one such experiment where corneal potentials were measured at two locations (Central and Inferior, cf. FIG. 2).

FIG. 5 shows a comparison of potentials measured at two locations on the cornea, Inferior and Central. Responses were evaluated at the peak of the a- and b-waves for three different stimulus geometries (Full Field, Lower Half of source illuminated, Upper Half of source illuminated) and two flash strengths (bright, 54 sc cd s $m^{-2}$; dim, 0.01 sc cd s $m^{-2}$), as indicated in the title of each plot. Each stimulus condition (geometry and strength) was presented 10 times; bars plot means, error bars plot one standard deviation. All pair-wise comparisons between electrode positions and stimulus geometries were significantly different ($p<0.05$ in all cases).

As can be seen, there is a significant difference in amplitude across stimulus geometries for each electrode location. In FIGS. 5a-5c, a comparison of potentials is measured at two locations on the cornea, Inferior and Central. Responses are evaluated at the peak of the a- and b- waves for three different stimulus geometries (Full Field, Lower Half of source illuminated, Upper Half of source illuminated) and two flash strengths (bright, 54 sc cd s $m^{-2}$; dim, 0.01 sc cd s $m^{-2}$), as indicated in the title of each plot. Each stimulus condition (geometry and strength) was presented 10 times; bars plot means, error bars plot one standard deviation. All pair-wise comparisons between electrode positions and stimulus geometries are significantly different ($p<0.05$ in all cases).

Comparison of Model and Measurements for Non-Uniform Retinal Activity. Experimental measurements and model predictions of corneal potentials at two locations were compared across three stimulus geometries, as shown in FIG. 6.

Figure 6:
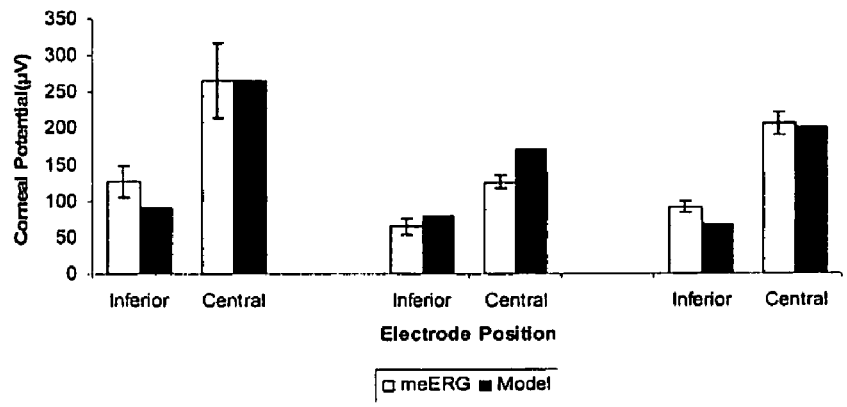
FIG. 6 shows a comparison of meERG potentials and model predictions.
Figure 6:
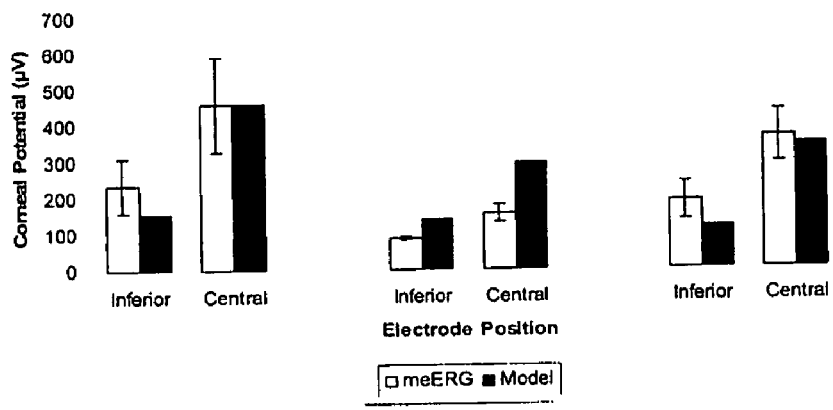
Figure 6:
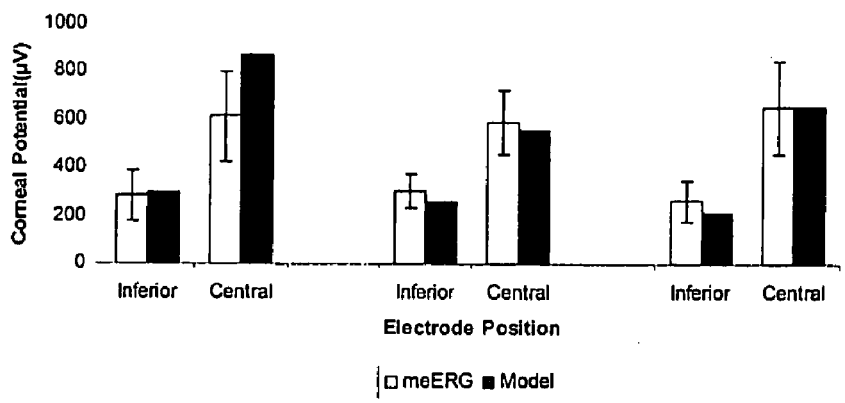

FIG. 6 shows a comparison of meERG potentials and model predictions. meERG responses were evaluated at the peak of the a- and b-waves for three different stimulus geometries (Full Field, Lower Half of source illuminated, Upper Half of source illuminated) and two flash strengths (bright, 54 sc cd s $m^{-2}$; dim, 0.01 sc cd s $m^{-2}$), as indicated in the title of each plot. Model predictions were normalized to the largest meERG potential in each panel. These results are from the first-approximation model, before any effort to optimize the model based on experimental results. The qualitative agreement is quite good, and will surely be improved in revised models, as described herein.

For simulations, the sinusoidal charge density on the vitreal surface of the retina is set to zero for either the superior half of the retina (simulating a Lower Half stimulus) or the inferior half of the retina (simulating an Upper Half stimulus). The agreement between the computed and measured meERG potentials at each location, under each stimulus condition, is quite good for this first-approximation model (model optimization is described herein) and the uncertain spatial variation of retinal illuminance in meERG experiments (see above).

Simulation of Percent (%) Functional Deficit. Most retinal pathologies do not result in immediate and complete lack of function in a given area, but rather a progressive decrease from normal. To estimate the % functional deficit that could be detected using meERG potentials, partial dysfunction was simulated in the inferior hemisphere by reducing the peak charge density on the retina in 10% increments, and potentials were evaluated at five locations on the cornea.

Figure 7:
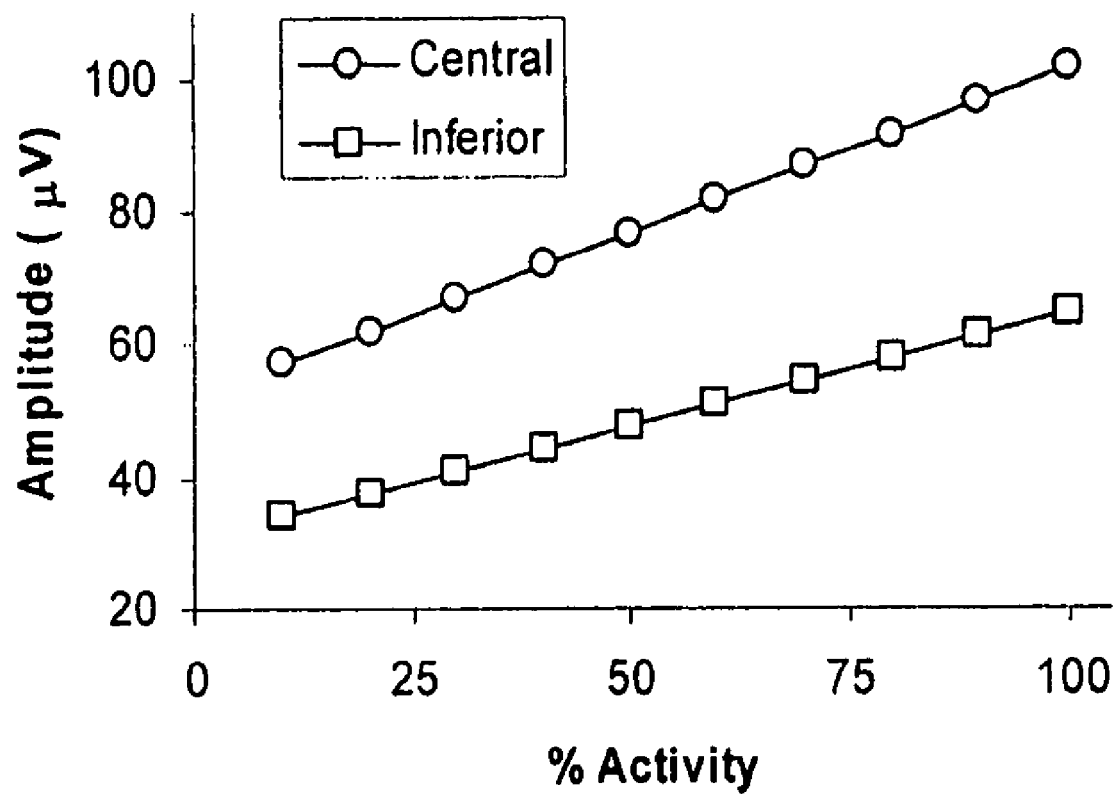
FIG. 7 shows a graphical representation of corneal potentials evaluated at two locations.

FIG. 7 shows a graphical representation of corneal potentials evaluated at two locations (Central and Inferior). The activity in the inferior half of the retina was attenuated (as described herein) in 10% increments. The slope of the best-fit lines for the Central and Inferior values were 4.9 and 3.3 mV (10% change)$^{-1}$ respectively. If typical noise levels are taken to be 5 µV, then a 10-20% level of dysfunction over a broad area of retina may be detected.

There is a near-linear relationship between the percentage of normal function and the predicted potentials at both locations, with slopes of 4.9 and 3.3 mV (10% change)$^{-1}$ at the Central and Inferior electrode locations, respectively. Typical RMS noise for a single meERG response waveform was measured to be 4.3 mV (10 randomly selected responses); this figure was reduced to 0.9 mV by averaging 10 responses. Thus, the present invention makes it possible to detect areas of very moderate loss of function.

The results described above demonstrate that the cornea is not isopotential, and that the potential at a given corneal location changes significantly and consistently for variations in retinal activity. This strongly suggests that the potential recorded at any one location on the cornea represents a sum of contributions of different spatial "units" of retinal tissue, where the weights of each retinal unit in the sum are unequal and independent of each other. Further, a first-approximation model is constructed which exhibits general qualitative agreement with measured meERG potentials.

As shown in Table 1, conductivity values for model structures are given. Most values are taken from the IFAC web site (see References). Values for the choroid, R-membrane, outer limiting membrane, and tear film are estimated to be equivalent to blood vessels, cortical matter, cortical matter and body fluid, respectively.

TABLE 1

| Tissue | Conductivity (S/m) |
| --- | --- |
| Sclera | 0.5028 |
| Choroid | 0.2779 |
| R-membrane | 0.109 |
| Retina | 0.5028 |
| Outer Limiting Membrane | 0.1 |
| Vitrous Humor | 1.5 |
| Anterior Humor | 1.5 |
| Lens | 0.3222 |
| Cornea | 0.422 |
| Tear Film | 1.5 |
| Adipose Tissue | 0.02081 |
| Air | 0 |

Advantages of a contact lens electrode include more stable impedance (due to more stable contact and hydration of the cornea-electrode interface), more stable positioning of the electrodes, and faster collection of meERG data using five simultaneous acquisition channels. A 0-diopter contact lens suitable for rat is molded from poly(methyl methacrylate) (PMMA) using a 6 or 8 mm glass ball lens as a form to accommodate the radius of curvature of the rat eye. Virtually any suitable material and construction technique can be used for the contact lens.

Care is taken to pattern the curved surface of the lens for selective metal deposition. The glass balls are also be used to fabricate polyamide masks to be used to pattern the inner surface of the contact lens electrode with transparent gold electrodes using the following procedure: The ball is spin-coated to a thickness of ~100 microns and the polyamide soft-baked; 750 micron diameter holes are manually cut for each of the five electrodes using a custom fabricated trephine; a trace line from the central electrode to the periphery is cut with a sapphire surgical knife under a dissecting microscope; and the mask carefully removed by hand. The mask is pressed into the inner surface of the contact lens (soft-baked polyamide adheres to PMMA with moderate physical pressure) and the outer surface masked with a painted-on coating of latex. The masked lens then receives a 50 Angstrom thick coating of gold (optically transparent yet sufficiently conductive [Hatton et al., 2003]) using E-beam metal evaporation, and the mask and protective latex peeled away. The trace line is insulated with hand application of a thin layer of PMMA. A layer of conductive epoxy makes contact with each electrode (and the gold trace from the central electrode) and wrap around the edge of the lens to the top surface, where leads of very fine wire are affixed to the lens, also via conductive epoxy. The hand-applied conductive epoxy is coated with hand-applied PMMA to avoid contact at the corneal margin.

The leading manufacturer of human and animal contact lens electrodes (Burien-Allen ERG electrodes), Hansen Labs, is not equipped to manufacture a rat-sized contact lens, or a lens with multiple contacts, or transparent gold electrodes. Construction experience is however gained by fabricating polyamide-based gold electrode arrays for implantation in the subretinal space of rats [Baig-Silva et al., 2005]. All of the basic fabrication steps described above are used in combination to produce a contact lens electrode array.

It should be appreciated that the array of electrodes does not necessarily need to be transparent; the array can comprise very narrow (fine) wires, which may be more cost effective. In either event, the electrode array is sufficiently open or transmissive so as to allow the passage of retinal illumination therethrough.

Figure 8:
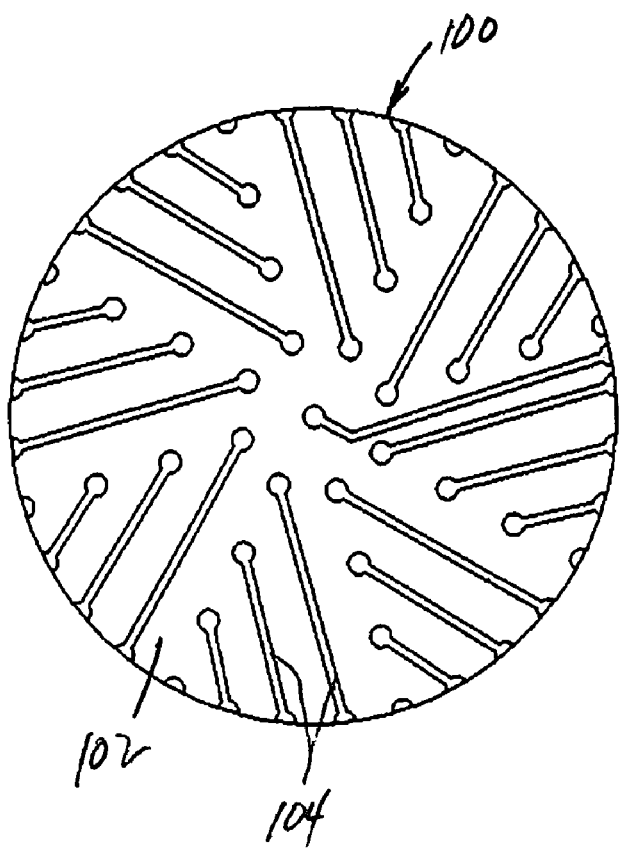
FIG. 8 shows a front elevational view of a contact lens assembly according to principles of the present invention.
Figure 9:
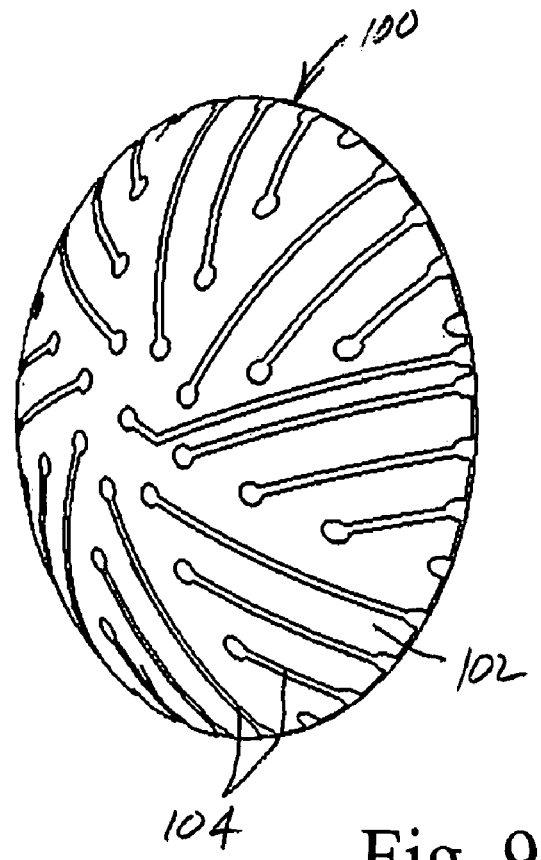
FIG. 9 shows a perspective view thereof.

Referring now to FIGS. 8-15, corneal contact lens assemblies and systems according to principles of the present invention, useful for humans and other species, are shown. Referring to FIGS. 8 and 9, a corneal contact lens assembly 100 includes a corneal contact lens base 102, which is preferably constructed of known materials, such as poly (methyl methacrylate) (PMMA), using known techniques. Virtually any material known today could be substituted as desired. Preferably, the contact lens base is plano-convex, having one curved surface which contacts the surface of the eye and a planar surface facing away from the eye, which would aid in introducing certain optical stimuli to the retina by eliminating the refractive power of the cornea. The contact lens body 102 provides a transparent substrate for carrying a plurality of electrodes applied to contact lens body 102 using known techniques, such as metal deposition. The electrodes may vary in material, including gold, platinum, iridium or other metals amenable to the fabrication process, or may be conductive polymers or doped silicon structures. As will be appreciated by those skilled in the art, contact lens assembly 100 can be scaled to virtually any size desired. The corneal contact lens assembly may be free to move relative to the cornea, or may be held in place by means of a speculum that extends under the eye lids.

As indicated in FIGS. 8 and 9, electrodes 104 are relatively thin and are spaced apart so as to allow a substantial amount of light to pass through the lens assembly 100. Put another way, even with a plurality of electrodes, such as the 33 circular integral electrodes shown in FIGS. 8 and 9, the contact lens assembly 100 is substantially transparent. The ability of light to pass the electrodes is due either to the thinness, and hence the transparency of the electrodes, or to their spacing, or both. If spacing is relied upon, it is important to note that because the electrode array on the contact lens is not in the focal plane of the eye, any shadows cast by opaque electrodes and conductive traces are blurred sufficiently at the surface of the retina so as to result in an approximately uniform decrease in retinal illuminance which will not hinder the meERG approach of this invention, which uses a uniform full-field stimulus. As indicated in FIGS. 8 and 9, connecting features from each electrode are preferably provided at the outer edge of the lens body. The connecting features may vary in material, including gold, platinum, iridium or other metals amenable to the fabrication process, or may be conductive polymers or doped silicon structures.

Figure 10:
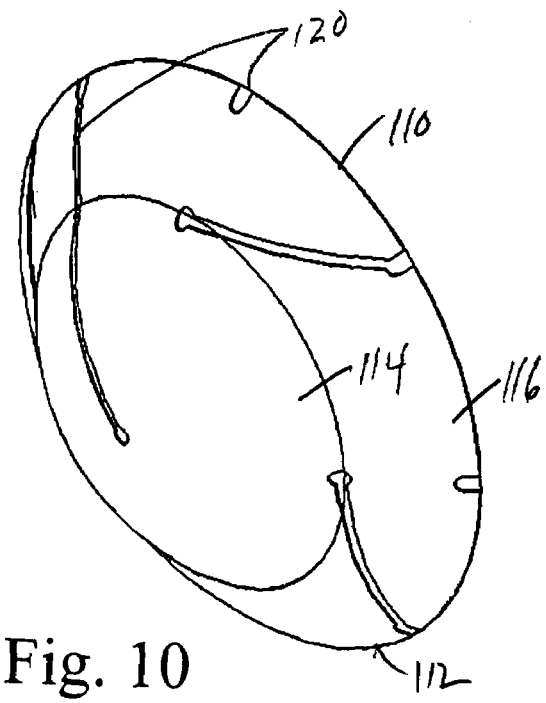
FIG. 10 shows a perspective view of another contact lens assembly according to principles of the present invention.
Figure 12:
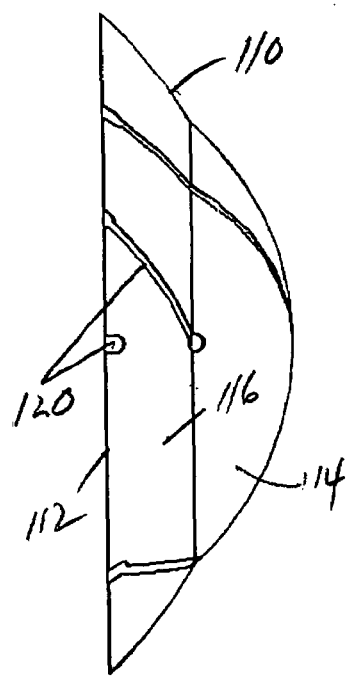
FIG. 12 shows a side elevational view thereof.
Figure 11:
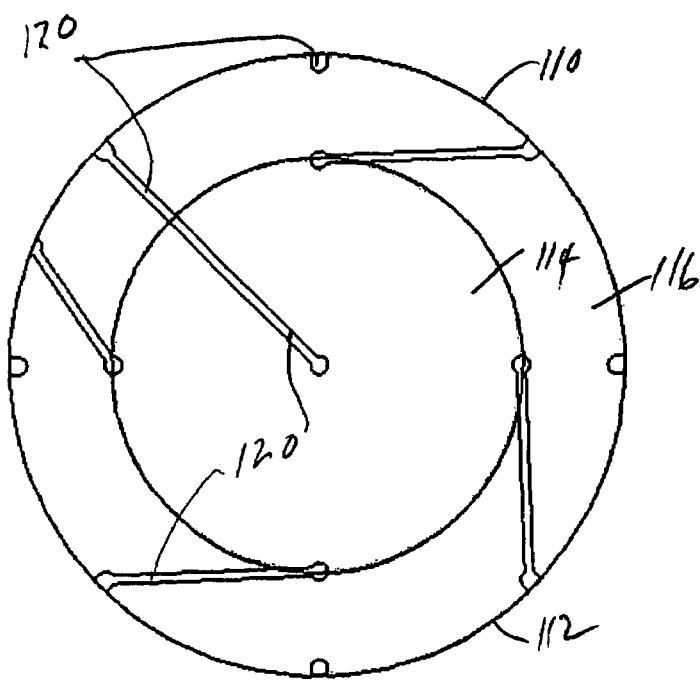
FIG. 11 shows a front elevational view thereof.

Referring to FIGS. 10-12, a contact lens assembly 110 includes a contact lens body 112 having an inner or central portion 114 of smaller radius and an outer concentric portion 116 of larger radius. Inner and outer portions 114, 116 are dimensioned to cover the cornea and the sclera, respectively. In the illustrated embodiment, nine electrodes 120 are provided, and extend to connecting features at the outer edge of the lens body.

Figure 13:
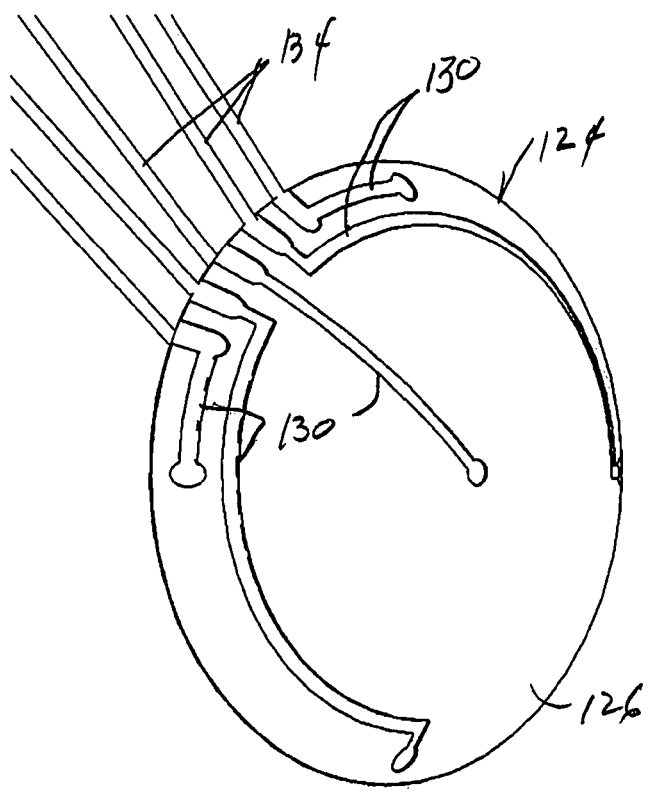
FIG. 13 shows a perspective view of a further contact lens assembly according to principles of the present invention.
Figure 14:
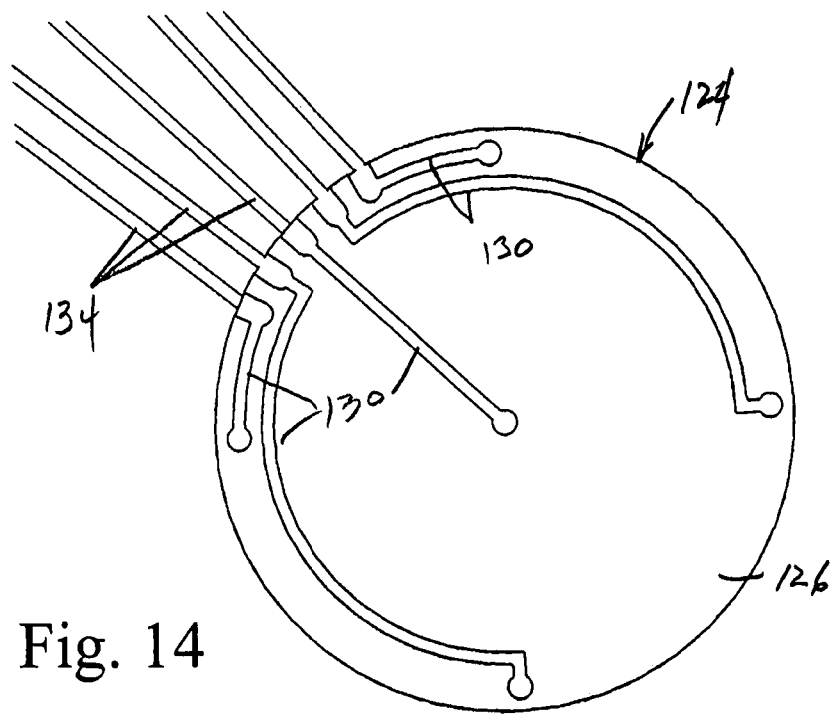
FIG. 14 shows a front elevational view thereof.

Referring to FIGS. 13 and 14, contact lens assembly 124 includes a contact lens body 126 carrying five integral electrodes 130. Note that one of the electrodes extends to the center of the lens body 126, while the remaining electrodes are generally curved, lying along concentric circular lines. The electrodes extend to the outer periphery of the lens body 126, where they are electrically connected to external wires 134 via a connecting feature integral to the lens.

Figure 15:
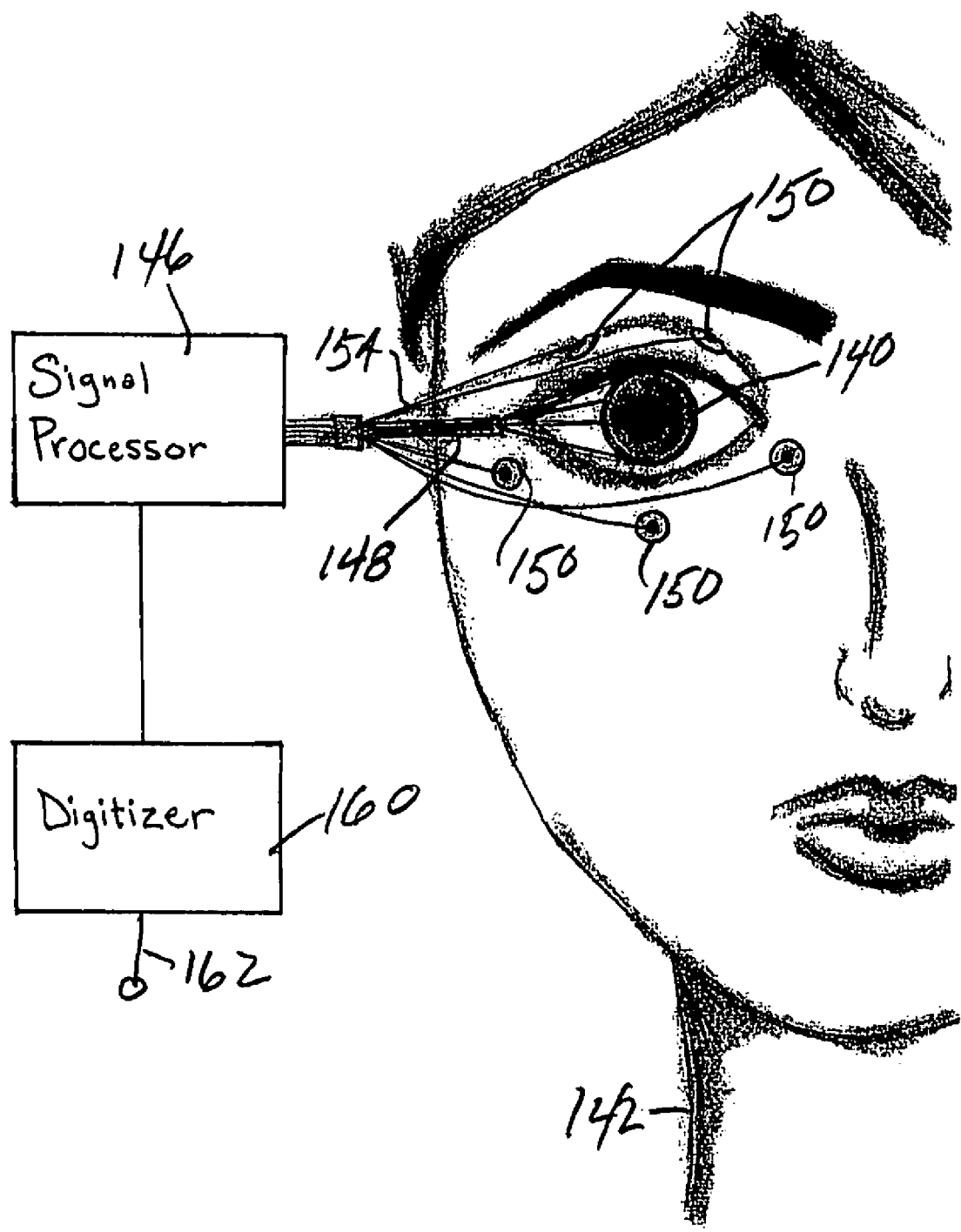
FIG. 15 shows a data collection system according to principles of the present invention.

Referring now to FIG. 15, a data collection system is shown in which a substantially transparent contact lens assembly 140 is fitted to a patient 142. The contact lens assembly may comprise any of the contact lens assemblies shown in FIGS. 8-14 herein, and preferably contains five electrodes coupled to a signal processor 146 by electrical leads 148. Five additional electrodes 150 are connected to portions of the skin surrounding the patient's eye. If desired, the skin electrodes can also be placed in contact with the scalp. Skin electrodes 150 are coupled to signal processor 146 by electrical leads 154. The electrodes and their connecting leads may be conveniently provided as a preassembled lead set, for use in the laboratory or in the field, as needed. Signal processor 146 contains filters and amplifiers appropriate for recording the electroretinogram, typically operating in a bandwidth of 0.1-500 Hertz, with a gain of 1000×. The processed signal(s) are preferably digitized at 160 for output on port 162 for storage and later analysis.

As can be seen from the above examples, electrodes are provided in the form of contact lens assemblies for electroretinographic recording. Included is a contact lens body having an outer periphery, an inner surface facing the patient's eye and an opposing outer surface. An array of conductive members, preferably five or more, is carried on the inner surface of the contact lens body so as to form an integral combination therewith. Preferably, the conductive members are narrow enough, and possibly thin enough, so as to be substantially transparent to illumination, such as full-field stimulation of the patient's eye.

The array of conductive members being positioned about the contact lens body so that at least a portion of the conductive members contacts the patient's cornea. If desired, the patient's sclera can also be contacted. It is generally preferred that the conductive members extend to the outer periphery of the contact lens body, and connections for electrically connecting the conductive members to electrical circuitry external to the electrode, are provided at the outer periphery.

Additional points of interest. The present invention provides a number of notable improvements to prior systems and methods. For example, the present invention provides a computational method of using the corneal potentials to determine local retinal activity useful in employing the meERG system described herein. Further, the present invention provides a finite-element model useful in performing this computational task.

The meERG technique of the present invention can be employed in a cost effective manner, by utilizing any of the specialized photic stimuli typically used with standard full-field ERG techniques. This novel use of these types of stimuli can be employed, for example, to provide information about function in specific retinal circuits or cell types that is not available from existing methods.

The present invention contemplates a computational method used to calculate, approximate or infer information about electrophysiological activity in the retina, especially regional differences in such activity, based on measurements of electrophysiological potentials made at the cornea. This computational method may include appropriate adaptations of any of the varied techniques developed for functional brain mapping based on electroencephalographic recordings, or those developed for mapping of cardiac activity based on measurements of cardiac potentials made at the surface of the heart or the torso, or any combination of elements of these techniques applied to solving for retinal potentials or currents based on knowledge of corneal potentials. With this computational method, retinal activity is determined from measurements of corneal potentials via an electrode array, as set out herein.

A finite-element model of the eye is provided, incorporating appropriate anatomical structures of the eye and surrounding tissues and materials, possibly including the contact lens electrode array described herein, and including the electrical properties of each structure in the eye. The model simulates retinal activity via a time-varying change in charge distribution or local currents within or across the retina, used in the above-described computational method of determining retinal activity from measurements of corneal potentials via an electrode array. This finite-element model of the eye is used in the determination of the optimum design of the contact lens electrode array inherent in the meERG approach as described here.

The present invention is also directed to the use of known photic stimuli which are designed to selectively elicit responses from specific cell types or functional pathways in the retina. These stimuli are used in conjunction with an array of corneal measurement electrodes as described above, such that local differences in function of these cell types or functional pathways can be obtained.

A system and method are provided by the present invention for obtaining information about the spatial distribution of photoreceptor activity and neural activity in the retina using simultaneously recorded multiple biopotential signals. In one example, the information thus gathered is used to assess retinal dysfunction due to trauma or disease. The biopotential signals are recorded from the surface of the eye and head using a plurality of electrodes, including those integral to a contact lens, as explained above and shown in FIGS. 8-15. The biopotential signals are recorded before, during and after the presentation of an optical stimulus to the subject eye. The recorded biopotential signals are then analyzed and interpreted to reveal the distribution of photoreceptor activity and neural activity across the retina. The analysis and interpretation of the biopotential signals is quantitative, and makes use of an electromagnetic model of the subject eye. The subject may be animal or human.

As can be seen from the above, the present invention, in certain aspects, employs a plurality of electrodes located on the surface of the eye, or the eye plus face and/or scalp. The electrodes record biopotentials generated by the retina in response to a light stimulus. The recorded biopotentials are then used to infer the spatial distribution of physiological activity in the retina of the subject. Solving for the spatial location and magnitude of electromagnetic sources from knowledge of field potentials recorded some distance from the source is referred to herein as source modeling, or solving the inverse problem. This technique has been applied for decades for the purpose of functional brain mapping and functional cardiac mapping, and is well known for that purpose. Here, analogous recording and computational approaches are applied to the eye, as explained above.

As mentioned, the present invention uses an array of recording electrodes integral to a contact lens, to record the electroretinogram biopotentials from the surface of the eye at multiple locations simultaneously. These eye-surface recordings may be augmented by additional surface potential recordings made from the face or scalp using conventional skin electrodes designed for this purpose.

A second central component of the current invention is the quantitative approach used to infer the spatial distribution of physiological activity in the retina from the measured surface potentials. As mentioned, this approach uses a detailed finite-element model of the subject eye, containing the proper anatomical and electrical properties of all major ocular tissues, including the tear film, cornea, aqueous humor, lens, vitreous humor, nerve fiber layer, retina, R-membrane, retinal pigment epithelium, choroid, sclera, and extraocular adipose tissue. Such models have been constructed for human and rat eyes, and can be adapted in a known manner, to any species for which appropriate anatomical information is available.

The model can be used, for example, in one of two ways. First, a library of surface potential distributions can be generated by simulating different locations and degrees of retinal dysfunction, and then the measured surface potentials are compared to the library. The closest match provides an estimate of the spatial extent and degree of retinal dysfunction. The second approach is to apply any of the many mathematical methods developed for the analogous goals of mapping brain function or cardiac function. These methods are reviewed in [He and Lian, 2002] and [He and Wu, 1999].

With the present invention, a finite-element model is used to solve for the location and magnitude of retinal source contributions to surface potentials recorded on the eye surface or eye and face. In contrast, previous attempts to relate spatial retinal potentials to spatial surface potentials used inadequate, very simple models and closed-form solutions to explore certain aspects of this field of research. Only the present invention relates spatial surface potentials to spatial retinal potentials using a substantially large number of surface electrodes. The resolution of the solution for retinal source potentials is directly related to the number of measurement locations, and the invention described here is adapted for use with five to five hundred, or more, recording electrodes.

PUBLICATIONS

Alexander K R, Fishman G A, Barnes C S, Grover S. *On-response deficit in the electroretinogram of the cone system in X-linked retinoschisis*. Invest Ophthalmol Vis Sci. 2001 February; 42(2):453-9.

Babiloni F, Cincotti F, Babiloni C, Carducci F, Mattia D, Astolfi L, Basilisco A, Rossini P M, Ding L, Ni Y, Cheng J, Christine K, Sweeney J, He B. *Estimation of the cortical functional connectivity with the multimodal integration of high-resolution EEG and fMRI data by directed transfer function*. Neuroimage. 2005 Jan. 1; 24(1):118-31.

Babiloni F. Mattia D. Babiloni C. Astolfi L. Salinari S. Basilisco A. Rossini P M. Marciani M G. Cincotti F. *Multimodal integration of EEG, MEG and fMRI data for the solution of the neuroimage puzzle*. Magn Reson Imaging. 2004 December; 22(10):1471-6.

Baig-Silva M S, Hathcock C D, Hetling J R. *A preparation for studying electrical stimulation of the retina in vivo in rat*. J Neural Eng. 2005 March; 2(1):S29-38. Epub 2005 Feb. 22.

Chan H H. *Detection of glaucomatous damage using multifocal ERG*. Clin Exp Optom. 2005 November; 88(6):410-4.

Davey K R, Thompson B, Wang S M, Koblasz A, Nation B. *Predicting Distributed Retinal Source Activity from ERG Data—Part I: Field Theoretical Approach*. IEEE Trans Biomed Eng. 1988 November; 35(11):942-7.

Doslak M J, Plonsey R, Thomas C W. *The effects of variations of the conducting media inhomogeneities on the electroretinogram*. IEEE Trans Biomed Eng. 1980 February; 27(2):88-94.

Edelman J L, Castro M R. *Quantitative analysis of laser-induced choroidal neovascularization in rat*. Exp Eye Res. 2000 November; 71(5):523-33.

Feigl B, Lovie-Kitchin J, Brown B. *Objective functional assessment of age-related maculopathy. a special application for the multifocal electroretinogram*. Clin Exp Optom. 2005 September; 88(5):304-12.

Hatton R A, Martin W R, Chestersa M A, *A robust ultrathin, transparent gold electrode tailored for hole injection into organic light-emitting diodes*. J. Mater. Chem., 2003, 13, 722-726.

He B. Lian J. *High-resolution spatio-temporal functional neuroimaging of brain activity*. Crit Rev Biomed Eng. 2002; 30(4-6):283-306.

He B. Wu D. *Laplacian electrocardiography*. Crit Rev Biomed Eng. 1999; 27(3-5):285-338.

Hetling J R, Pepperberg D R. *Sensitivity and kinetics of mouse rod flash responses determined in vivo from paired-flash electroretinograms*. J Physiol. 1999 Apr. 15; 516 (Pt 2):593-609.

Holder G E. *Electrophysiological assessment of optic nerve disease*. Eye. 2004 November; 18(11):1133-43.

Hood D, Wladis E, Shady S, Holopigian K, Li J, Seiple W. Multifocal rod electroretinograms. Invest Ophthalmol Vis Sci. 1998 June; 39(7):1152-62.

Hood D C, Frishman L J, Saszik S, Viswanathan S. *Retinal origins of the primate multifocal ERG: implications for the human response*. Invest Ophthalmol Vis Sci. 2002 May; 43(5):1673-85.

Hughes, A. "A Schematic Eye for the Rat," Vision Research, vol 19. pp 569-588, © Pergamon Press, Ltd. 1979.

IFAC, Italian National Resource Councel, "Nello Carara," Florence, Italy, http://niremf.ifac.cnr.it/tissprop/.

Lam, Byron L., Electrophysiology of Vision: Clinical Testing and Applications. Taylor & Francis, Boca Raton, 2005.

Montes-Mico R, Alio J L, Charman W N. *Postblink Changes in the Ocular Modulation Transfer Function Measured by a Double-Pass Method*. Invest Ophthalmol Vis Sci. 2005 December; 46(12):4468-73.

Plonsey, R. *Quantitative formulations of electrophysiological sources of potential fields in volume conductors*. IEEE Trans Biomed Eng. 1984 December; 31(12): 868-72.

Seiple W, Clemens C J, Greenstein V C, Carr R E, Holopigian K. *Test-retest reliability of the multifocal electroretinogram and humphrey visual fields in patients with retinitis pigmentosa*. Doc Ophthalmol. 2004 November; 109(3):255-72.

Silva, G A. Pepperberg, D R. *Step Response of Mouse Rod Photoreceptors Modeled in Terms of Elemental Photic Signals*. IEEE Trans Biomed Eng. 2004 January; 51(1): 3-12.

Tyrberg M, Ponjavic V, Lovestam-Adrian M. *Multifocal Electroretinography (mfERG) in Insulin Dependent Diabetics with and without Clinically Apparent Retinopathy*. Doc Ophthalmol. 2005 March; 110(2-3):137-43.

Cringle S J and Alder V A (1987), Current Eye Research 6(9):1109-1114

Cringle et al. (1986), Current Eye Research 5(12):959-965

Doslak et al. (1981), Med. & Biol. Eng. & Comp. 19:149-156

Gouras et al. (1962), Investigative Ophthalmology 1(3): 333-339

Job H M et al., (1999), Med. & Biol. Eng. & Comp. 37:710-719

Krakau C E T (1959), Acta Ophthalmologica 36(11):183-207

The foregoing description and the accompanying drawings are illustrative of the present invention. Additional variations and arrangements of parts are possible without departing from the spirit and scope of this invention.

What is claimed is:

1. An electrode array for electroretinography comprising:
a contact lens body having an outer periphery, an inner surface facing a patient's eye and an opposing outer surface;
an array of a plurality of conductive members carried on the inner surface of the contact lens body so as to be integral therewith;
multiple groups of linear conductive members being positioned about the contact lens body with different groups pointing in different directions so that at least a portion of the conductive members contacts the patient's cornea;
the array of conductive members being spaced apart from one another so as to be substantially transparent to full-field stimulation of the patient's eye;
the conductive members extending to the outer periphery of the contact lens body; and
connections for electrically connecting the conductive members to electrical circuitry external to the electrode for monitoring the array of conductive members at multiple locations, simultaneously, for the distribution of electrical activity of the retina as recorded at multiple locations across the cornea in response to the full-field stimulation, each connection being provided at the outer periphery so as to be integral with the contact lens body.

2. The electrode array of claim 1 wherein the conductive members have different lengths.

3. The electrode array of claim 1 wherein the conductive members extending from the outer periphery, generally toward the center.

4. The electrode array of claim 1 wherein the conductive members are elongated and spaced apart sufficiently so as to avoid substantially impairing the patient's vision.

5. An electrode array for electroretinography comprising:
a contact lens body having an outer periphery, an inner surface facing a patient's eye and an opposing outer surface, with a plurality of concentric reference circles on the inner surface;
an array of a plurality of conductive members carried on the inner surface of the contact lens body so as to be integral therewith, pointing in different directions and extending to an inner one of the concentric circles so that at least a portion of the conductive members contacts the patient's cornea;
a central conductive member carried on the inner surface of the contact lens body so as to be integral therewith, extending to the approximate center of the contact lens body;
the array of conductive members being spaced apart from one another so as to be substantially transparent to full-field stimulation of the patient's eye;
the conductive members extending to the outer periphery of the contact lens body; and
connections for electrically connecting the conductive members to electrical circuitry external to the electrode for monitoring the array of conductive members at multiple locations, simultaneously, for the distribution of electrical activity of the retina as detected at multiple locations across the cornea in response to the full-field stimulation, each connection being provided at the outer periphery so as to be integral with the contact lens body.

6. The electrode array of claim 5 wherein the conductive members have different lengths.

7. The electrode array of claim 5 wherein the conductive members extending from the outer periphery, generally toward the center.

8. The electrode array of claim 5 wherein the conductive members are elongated and spaced apart sufficiently so as to avoid substantially impairing the patient's vision.

9. An electrode array for electroretinography comprising:
a contact lens body having an outer periphery, an inner surface facing a patient's eye and an opposing outer surface, with a plurality of concentric reference circles adjacent the outer periphery;
an array of a plurality of conductive members carried on the inner surface of the contact lens body so as to be integral therewith, including two pairs of part circular elements adjacent the outer periphery, extending away from one another, with the elements of each pair having a different length;
a central conductive member carried on the inner surface of the contact lens body so as to be integral therewith, extending to the approximate center of the contact lens body;
the array of conductive members and the central conductive member being spaced apart from one another so as to be substantially transparent to full-field stimulation of the patient's eye; and
connections for electrically connecting the conductive members to electrical circuitry external to the electrode for monitoring the array of conductive members at multiple locations simultaneously for the distribution of electrical activity of the retina as observed at multiple locations across the cornea in response to the full-field stimulation, each connection being provided at the outer periphery so as to be integral with the contact lens body.

10. The electrode array of claim 9 wherein the conductive members have a uniform width.

11. The electrode array of claim 9 wherein the conductive members extending from the outer periphery, generally toward the center.

12. The electrode array of claim 9 wherein the conductive members are elongated and spaced apart sufficiently so as to avoid substantially impairing the patient's vision.

* * * * *